(12) United States Patent
Hu et al.

(10) Patent No.: US 11,084,816 B2
(45) Date of Patent: Aug. 10, 2021

(54) ANIONIC IMIDE MATERIAL HAVING FERROMAGNETISM AT ROOM TEMPERATURE AND THE USE THEREOF

(71) Applicant: South China University Of Technology, Guangdong (CN)

(72) Inventors: Dehua Hu, Guangdong (CN); Qinglin Jiang, Guangdong (CN); Yuguang Ma, Guangdong (CN); Duokai Zhao, Guangdong (CN); Jiang Zhang, Guangdong (CN); Zhongquan Mao, Guangdong (CN); Yao Yao, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 16/496,394

(22) PCT Filed: Jul. 25, 2018

(86) PCT No.: PCT/CN2018/096929
§ 371 (c)(1),
(2) Date: Sep. 20, 2019

(87) PCT Pub. No.: WO2019/134360
PCT Pub. Date: Jul. 11, 2019

(65) Prior Publication Data
US 2020/0247802 A1 Aug. 6, 2020

(30) Foreign Application Priority Data

Jan. 5, 2018 (CN) .......................... 201810010993.9
May 10, 2018 (CN) .......................... 201810444533.7

(51) Int. Cl.
*C07D 471/06* (2006.01)
*H01F 1/42* (2006.01)

(52) U.S. Cl.
CPC ............. *C07D 471/06* (2013.01); *H01F 1/42* (2013.01)

(58) Field of Classification Search
CPC ... C07D 487/06; C07D 471/06; C07D 487/08
See application file for complete search history.

(56) References Cited

FOREIGN PATENT DOCUMENTS

| CN | 101414134 A | | 4/2009 |
|---|---|---|---|
| CN | 101508893 A | | 8/2009 |
| CN | 102057015 A | | 5/2011 |
| CN | 102583235 A | * | 7/2012 |
| CN | 105670286 A | | 6/2016 |
| CN | 108063180 A | | 5/2018 |

OTHER PUBLICATIONS

English tranlation of CN 102583235 Am sections [0001]-[0098]. (Year: 2012).*
Zhang et al., "Preparation and, etc.," Science China Chem., 60 (10) 1334-1339. (Year: 2017).*
Iron et al. "On the Unexpected, etc.," J. Phys. Chem. A, 115, 2047-2056. (Year: 2011).*
WIPO, Chinese International Search Authority, International Search Report (with English Translation) and Written Opinion dated Oct. 24, 2018 in International Patent Application No. PCT/CN2018/096929, 8 pages.

* cited by examiner

*Primary Examiner* — Patricia L Morris
(74) *Attorney, Agent, or Firm* — Masuvalley & Partners

(57) ABSTRACT

The anionic imide material is obtained by preparing a solution or a suspension of an imide compound, then reducing and drying the same; the anionic material comprises anions of an imide compound, the anions being at least one selected from the following formula I or formula II; in formula I or II: n=1, 2, or 3; $R_1$, $R_2$ are respectively selected from at least one of H, amino, carboxyl, hydroxy, thiol, and pyridyl groups; $X_1$-$X_4$ are respectively an electron withdrawing group, and specifically selected from one of H, F, Cl, Br, CN, and $NO_2$ groups. The anionic material of the present invention has a Curie temperature larger than room temperature and ferromagnetism, and is an organic magnetic material; it may be used for preparing an organic magnetic material and/or an organic magnetic device.

8 Claims, 2 Drawing Sheets

ANIONIC IMIDE MATERIAL HAVING FERROMAGNETISM AT ROOM TEMPERATURE AND THE USE THEREOF

RELATED APPLICATIONS

This application is the U.S. National Phase of and claims priority to International Patent Application No. PCT/CN2018/096929, International Filing Date Jul. 25, 2018, entitled An Imide-Type Compound Anionic Material Having Room-Temperature Ferromagnetism And Application Thereof, which claims benefit of Chinese Patent Application No. 201810010993.9 filed Jan. 5, 2018 and Chinese Patent Application No. 201810444533.7 filed May 10, 2018; all of which are incorporated herein by reference in their entireties.

TECHNICAL FIELD

The present invention belongs to the technical field of organic magnetic materials, specifically relates to an anionic imide material having ferromagnetism at room temperature and the use thereof. The anionic imide material is ferromagnetic at room temperature and may be used for organic magnetic materials and preparing organic magnetic device.

BACKGROUND ART

Conventional magnets are usually composed of transition metals with unpaired d or f electrons and their oxides or rare earth elements, and are inorganic magnetic materials. The development of organic magnets has been a hot topic in the fields of physics, chemistry and material science. An organic material usually has only covalently bonded s and p electrons and does not have unpaired electrons. Therefore, in general, organic materials are not paramagnetic or ferromagnetic. Magnetic properties can also be provided in some organic materials by introducing magnetic metal atoms/ions or generating radicals having a single electron occupying orbital. Organic magnetic compounds include pure organic magnetic compounds and metal-containing organic magnetic compounds depending on whether or not metal atoms or ions are contained in the structure. The pure organic magnetic compounds refer to organic magnets which do not contain a transition metal or a rare earth element. Although some organic magnets have been developed at present, the existing organic magnets have a ferromagnetic Curie temperature at a low temperature, the maximum of which is not higher than 36 K. Although organic magnets with higher Curie temperatures were later found in organic charge transfer salts and metal complexes, the synthesis of pure organic magnets at room temperature without metals remains a significant challenge.

SUMMARY OF THE INVENTION

In order to overcome the deficiencies and disadvantages of the prior art, an object of the present invention is to provide an anionic imide material. The present invention prepares anions of the imide compound (monovalent anion and/or divalent anion) so as to obtain a pure organic magnetic material with high performance.

Another object of the present invention is to provide the use of the anionic imide material. The imide compound anion material is used as an organic magnetic material. The anionic imide material of the invention is ferromagnetic, has a Curie temperature higher than room temperature and a coercive force of about 200 Oe, thereby providing a basis for preparing a high performance pure organic magnetic device. The anionic imide material of the present invention may be used to prepare an organic magnetic device.

The object of the invention is achieved by the following technical solutions:

An anionic imide material comprises anions of a reduced imide compound, the anions being at least one selected from the following formula I or formula

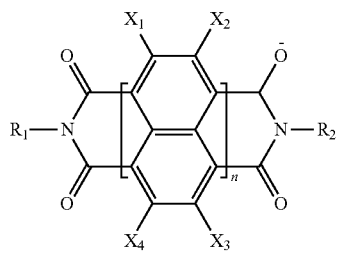

Formula I

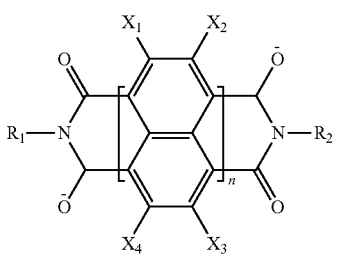

Formula II where in formula I or II: n=1, 2, or 3; $R_1$, $R_2$ are respectively selected from at least one of H, amino, carboxyl, hydroxy, thiol, and pyridyl groups;

$X_1$-$X_4$ are respectively an electron withdrawing group, and specifically selected from one of H, F, Cl, Br, CN, and $NO_2$ groups.

The anionic imide material is obtained by preparing a solution or a suspension of an imide compound, reducing the same to obtain a solution or a suspension of an anionic imide compound, and then drying the solution or the suspension of the anionic imide compound; said reduction refers to reducing the imide group to an anion;

the structure of the imide compound is as follows:

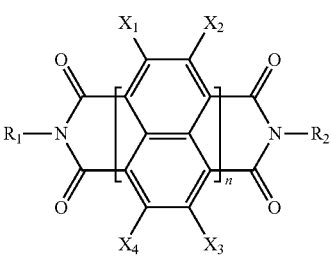

Formula III where in the formula: n=1, 2, or 3; $R_1$, $R_2$ are respectively selected from at least one of H, amino, carboxyl, hydroxy, thiol, and pyridyl groups;

$X_1$-$X_4$ are respectively an electron withdrawing group, and specifically selected from one of H, F, Cl, Br, CN, and $NO_2$ groups.

The anionic imide material is obtained by reducing the imide compound in a solvent to obtain a solution or a suspension of an anionic imide compound, and then drying the solution or the suspension of the anionic imide compound.

The solution or the suspension of the imide compound is prepared by the following method:

mixing the imide compound with hydrazine hydrate for reduction to obtain the solution or the suspension of the anionic imide compound.

The imide compound has a concentration of 1-50 mg/mL in hydrazine hydrate.

The reduction is carried out under heating and/or pressurization condition.

The heating is carried out under 50-200° C., and the pressurization is carried out under 2-32 MPa.

The time of the reduction is 10-48 h.

Or the solution or the suspension of the anionic imide compound is obtained by mixing the imide compound with an organic solvent and adding a reducing agent for reduction.

The reduction is carried out under −10-160° C. for 0.1 h-48 h, preferably for 5-48 h;

The amount of the reducing agent is determined according to the characteristics of the reducing agent. If one equivalent of the reducing agent may reduce one equivalent of the imide (imide group in the imide compound) to a divalent anion, the amount of the reducing agent should be 1-10 equivalents; if two equivalents of the reducing agent are required to reduce one equivalent of the imide to a divalent anion, the amount of the reducing agent should be 2-10 equivalents.

The concentration of the imide compound in the organic solvent is 1-50 mg/mL.

The organic solvent is at least one of N,N-dimethylformamide, N,N-dimethylacetamide, dimethyl sulfoxide, tetrahydrofuran, chloroform, dichloromethane, toluene, chlorobenzene, o-dichlorobenzene, ethyl acetate, methanol, acetone, acetonitrile, ethylene glycol dimethyl ether, 1,2-dichloroethane, dioxane, pyridine and 2-methylpyrrolidone.

The reducing agent is at least one of an alkali metal, hydrazine hydrate, sodium dithionite, sodium sulfide, and potassium sulfide. The alkali metal includes Lithium, Sodium and Potassium, etc.

Or the solution or the suspension of the anionic imide compound is obtained by mixing the imide compound with an organic solvent and applying a bias voltage for electrochemical reduction.

The electrochemical reduction lasts for 1 s-10 min, and the bias voltage is 0 to −2.5 V.

The organic solvent is at least one of N,N-dimethylformamide, N,N-dimethylacetamide, dimethyl sulfoxide, tetrahydrofuran, chloroform, dichloromethane, toluene, chlorobenzene, o-dichlorobenzene, ethyl acetate, methanol, acetone, acetonitrile, ethylene glycol dimethyl ether, 1,2-dichloroethane, dioxane, pyridine and 2-methylpyrrolidone.

The concentration of the imide compound in the organic solvent is 1-50 mg/m L.

The anionic imide material is obtained by drying the solution or suspension of the anionic imide compound. The drying is preferably by heating.

The anionic imide material is a film or a powder, which is obtained by processing the solution or suspension of the anionic imide compound by a common technique, preferably by spin coating, brush coating, spray coating, dip coating, roll coating, screen printing, printing, or ink jet printing to form a film or a powder on a substrate.

The anionic imide material of the present invention is ferromagnetic at room temperature, and may be used as an organic magnetic material.

An organic magnetic material comprises the anionic imide material as mentioned above.

Preferably, the organic magnetic material is the anionic imide material. The anionic imide material may be used for preparing an organic magnetic device.

The material of the present invention exhibits better performance as an organic magnetic material. The imide material selected by the invention has a large conjugate plane structure, wherein the molecules pack orderly with small intermolecular spacing so that the interaction is strong and the radicals are arranged in an orderly manner to generate magnetic moment; also the presence of four electron-withdrawing carbonyl groups in the molecule enables the molecule to become a stable monovalent and divalent anion. The anionic material can be constructed to comprise divalent anions as a main component and free radical anions as a small amount of dopant, which shows ferromagnetism near room temperature and apparently higher Curie temperature of ferromagnetic transition (Tc=400 K) than that of the reported organic magnets with a coercive force close to 200 Oe at room temperature.

The imide compound has good chemical, thermal and light stability and a large conjugated skeleton, which can be widely used in organic solar cells, electroluminescent devices, field effect transistors, self-assembly and bio-fluorescence detectors. Due to the strong intermolecular interaction and small intermolecular spacing, the imide compound can achieve ferromagnetic coupling. The invention provides an anionic imide material with ferromagnetism at room temperature, and has broad application prospects in pure organic magnetic materials and devices.

Compared with the prior art, the present invention has the following advantages and benefits:

(1) The imide compound of the present invention has ferromagnetism with a Curie temperature higher than room temperature and a large coercive force, which is a pure organic magnetic material at room temperature and has a broad application prospect;

(2) The invention uses a solution processing technique so that the preparation process is simple and the production cost is low.

DETAILED DESCRIPTION OF EMBODIMENTS

The present invention will be further described in detail below with reference to the embodiments and drawings, but the embodiments of the present invention are not limited thereto. The anionic imide material of the present invention contains anions after reduction of an imide compound, and further contains cations which match with the anions.

Example 1

A perylene bisimide derivative (N,N-dihydro-1,6,7,12-tetrachloro-3,4,9,10-tetracarboxyl perylene bisimide) of the present embodiment has the following structure:

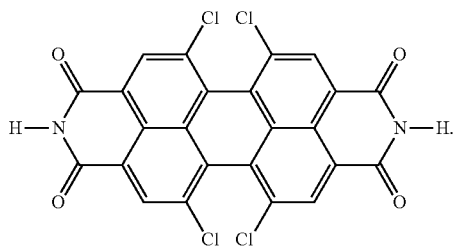

Figure 1:
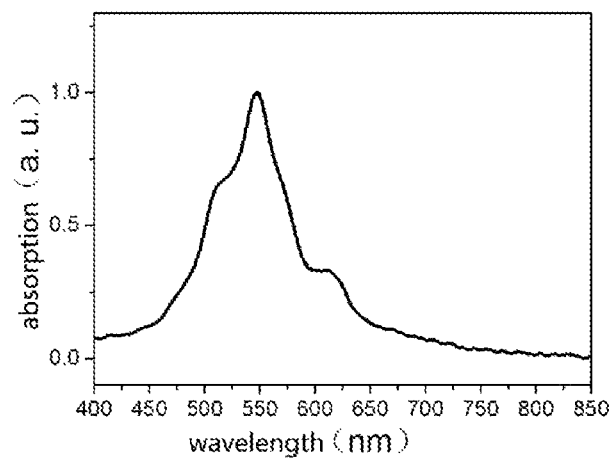
FIG. 1 is a UV-Vis absorption spectrum of a solution of perylene bisimide anions prepared in Example 1.

Preparation of a solution of perylene bisimide anions: 100 mg of N,N-dihydro-1,6,7,12-tetrachloro-3,4,9,10-tetracarboxyl perylene bisimide (Reference: J. Org. Chem., 2011, 76, 2386-2407) was added to 15 mL of hydrazine hydrate solvent (80% by volume), the lid of the reactor used was tightened, the reactor was placed in an oven, then the temperature was raised to 140° C. to react for 24 h. After the reaction, the mixture was cooled to room temperature, the reactor was transferred to a nitrogen glove box, the lid was opened, and the liquid therein was filtered through a 0.45 um organic phase filter to obtain the solution of perylene bisimide anions (purine solution of perylene bisimide divalent anions). The UV-Vis absorption spectrum of the solution of perylene bisimide anions (solution of perylene bisimide divalent anions) prepared in this example is shown in FIG. 1.

Figure 2:
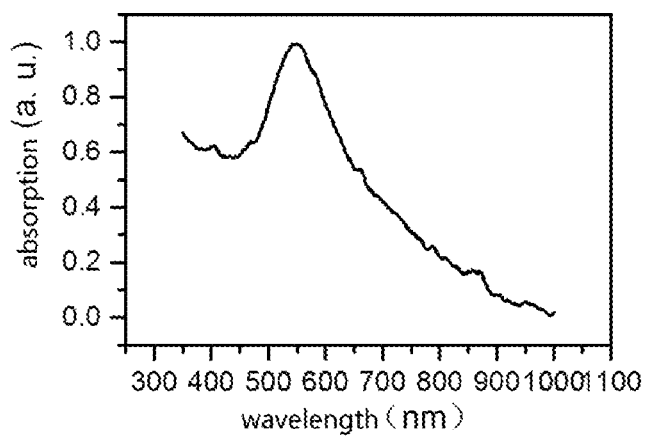
FIG. 2 is a UV-Vis absorption spectrum of a perylene bisimide anion film prepared in Example 1.
Figure 4:
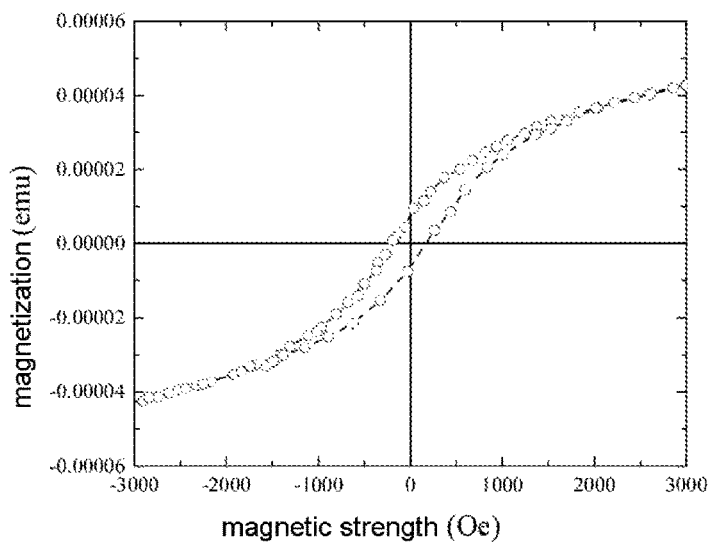
FIG. 4 is a hysteresis loop diagram of a perylene bisimide material prepared in Example 1 on the surface of a high-purity silicon wafer at 300 K.
Figure 5:
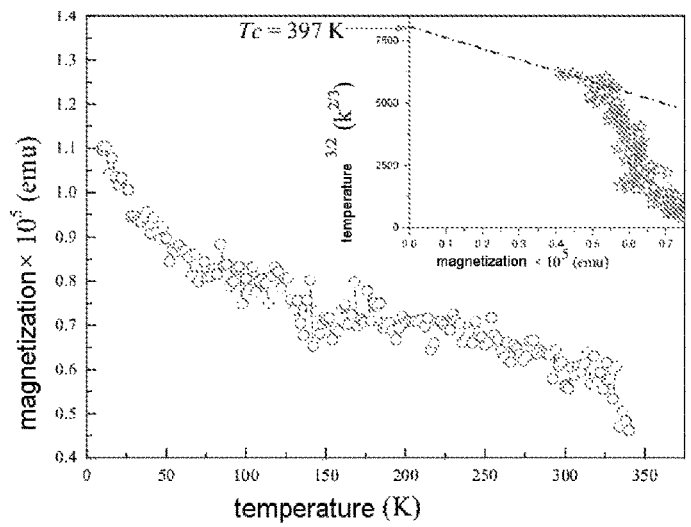
FIG. 5 is a curve plotting the magnetization of a perylene bisimide imide material prepared in Example 1 against temperature; the upper right graph is obtained by fitting the curve according to the Bloch equation to obtain the Curie temperature.

Preparation of an Anionic Perylene Bisimide Material:

(1) The surface of a quartz substrate was cleaned by ultrasonic treatment with acetone, detergent dedicated for micron-sized semiconductor, deionized water and isopropanol in sequence for 10 minutes, and then the substrate was placed in a constant temperature oven at 80° C. for 4 hours for drying;

(2) The cleaned quartz substrate was transferred to the nitrogen glove box and placed horizontally. An appropriate amount of the solution of perylene bisimide anions was dripped onto the quartz substrate by pipetting; then it was heated at 80° C. for 15 min to obtain a flattened divalent anionic perylene bisimide material (anionic perylene bisimide material (film)) having a thickness of 300 nm-5 μm. The UV-Vis absorption spectrum of the anionic perylene bisimide material (divalent anionic perylene bisimide material) prepared in this example is shown in FIG. 2. The anionic perylene bisimide material prepared in this example exhibits a coercive force of 188 Oe on the surface of a high-purity silicon wafer as shown by the hysteresis loop at 300K in FIG. 4, which indicates obvious ferromagnetism thereof. A curve plotting the magnetization of the anionic perylene bisimide material prepared in this example against temperature is shown in FIG. 5. By fitting the curve plotting the magnetization of the anionic perylene bisimide material (sample) against temperature under 1000 Oe according to the Bloch equation $(Ms(T)/Ms(0)=1-bT^{1.5})$, the Curie temperature of the sample is found to be near 400 K. With reference to FIG. 4 and FIG. 5, the present invention successfully obtains a pure organic material ferromagnetic at room temperature. Performance of the anionic perylene bisimide material of this example is shown in Table 1.

TABLE 1

Performance of the anionic perylene bisimide material of example 1

| Sample | Coercive force (Oe) | Curie Temperature (K) |
|---|---|---|
| Example 1 | 188 | 397 |

Example 2

A perylene bisimide derivative (N,N-dihydro-3,4,9,10-tetracarboxyl perylene bisimide) of the present embodiment has the following structure:

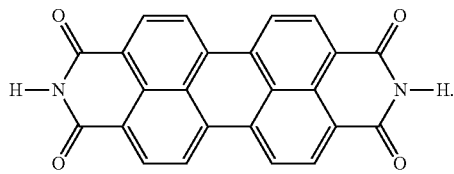

Preparation of a solution of perylene bisimide anions: 100 mg of N,N-dihydro-3,4,9,10-tetracarboxyl perylene bisimide was added in a reactor, 15 mL of hydrazine hydrate solvent (80% by volume) is further added, the lid of the reactor used was tightened, the reactor was placed in an oven, then the temperature was raised to 140° C. to react for 24 h. After the reaction, the mixture was cooled to room temperature, the reactor was transferred to a nitrogen glove box, the lid was opened, and the liquid therein was filtered through a 0.45 um organic phase filter to obtain the solution of perylene bisimide anions (purine solution of perylene bisimide divalent anions).

Preparation of an anionic perylene bisimide material (divalent anionic perylene bisimide material):

The preparation is the same as that of Example 1.

By fitting a curve plotting the magnetization of the anionic perylene bisimide material (PBI material) against temperature under 1000 Oe, the Curie temperature of the PBI material is obtained and shown in Table 2.

TABLE 2

Performance of the anionic perylene bisimide material of example 2

| Sample | Coercive force (Oe) | Curie Temperature (K) |
|---|---|---|
| Example 2 | 142 | 283 |

Figure 3:
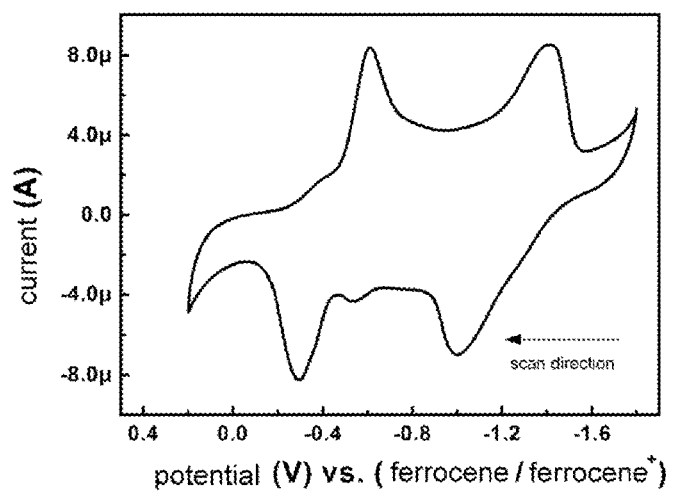
FIG. 3 is a cyclic voltammetry curve of a neutral solution of a perylene bisimide derivative in Example 2.

The perylene bisimide derivative (N,N-dihydro-3,4,9,10-tetracarboxyl perylene bisimide) of the present example was prepared to be a neutral solution (adding 1 mg of N,N-dihydro-3,4,9,10-tetracarboxyl perylene bisimide to 10 mL of dichloromethane solvent, stirring at room temperature for 30 min, cooling and allowing the solution to stand, wherein the supernatant is the neutral solution). A cyclic voltammetry curve of the neutral solution of the perylene bisimide derivative of the present example is shown in FIG. 3.

The above embodiments are preferred embodiments of the present invention, but the embodiments of the present invention are not limited thereto, and any other changes, modifications, substitutions, combinations and simplifications made without departing from the spirit and scope of the present invention are equivalent means, and are included in the scope of protection of the present invention.

The invention claimed is:

1. An anionic imide material, anions of the anionic imide material being at least one selected from the following formula I or formula II;
where in formula I or II: n=1, 2, or 3; $R_1$, $R_2$ are respectively selected from at least one of amino, carboxyl, hydroxy, thiol, and pyridyl groups; and $X_1$-$X_4$ are selected from one of CN, and $NO_2$ groups

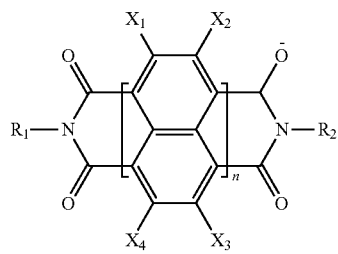

Formula I

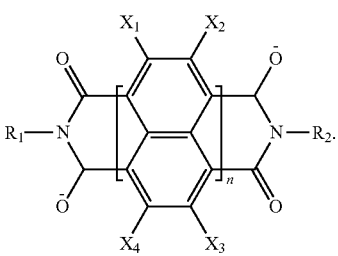

Formula II

2. A method for preparing the anionic imide material according to claim 1, comprising: preparing a solution or a suspension of an imide compound, reducing the same to obtain a solution or a suspension of an anionic imide compound, and then drying the solution or the suspension of the anionic imide compound; said reduction refers to reducing the imide group to an anion;
the structure of the imide compound is as follows:

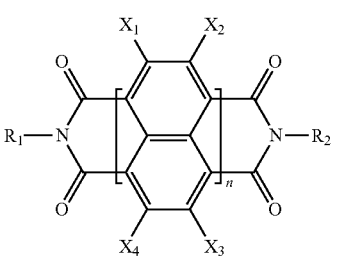

Formula III where in the formula: n=1, 2, or 3; $R_1$, $R_2$ are respectively selected from at least one of amino, carboxyl, hydroxy, thiol, and pyridyl groups;
$X_1$-$X_4$ selected from one of CN, and $NO_2$ groups.

3. The method according to claim 2, wherein the solution or the suspension of the imide compound is prepared by the following method:
mixing the imide compound with hydrazine hydrate for reduction to obtain the solution or the suspension of the anionic imide compound.

4. The method according to claim 3, wherein the imide compound has a concentration of 1-50 mg/mL in hydrazine hydrate;
the reduction is carried out under heating and/or pressurization condition;
the heating is carried out under 50-200° C., and the pressurization is carried out under 2-32 MPa;
the time of the reduction is 10-48 h.

5. The method according to claim 2, wherein the solution or the suspension of the anionic imide compound is obtained by mixing the imide compound with an organic solvent and adding a reducing agent for reduction.

6. The method according to claim 5, wherein the reduction is carried out under −10-160° C. for 0.1 h-48 h;
the concentration of the imide compound in the organic solvent is 1-50 mg/mL;
the organic solvent is at least one of N,N-dimethylformamide, N,N-dimethylacetamide, dimethyl sulfoxide, tetrahydrofuran, chloroform, dichloromethane, toluene, chlorobenzene, o-dichlorobenzene, ethyl acetate, methanol, acetone, acetonitrile, ethylene glycol dimethyl ether, 1,2-dichloroethane, dioxane, pyridine and 2-methylpyrrolidone;
the reducing agent is at least one of an alkali metal, hydrazine hydrate, sodium dithionite, sodium sulfide, and potassium sulfide.

7. The method according to claim 2, wherein the solution or the suspension of the anionic imide compound is obtained by mixing the imide compound with an organic solvent and applying a bias voltage for electrochemical reduction.

8. The method according to claim 7, wherein the electrochemical reduction lasts for 1 s-10 min, and the bias voltage is 0 to −2.5 V;
the organic solvent is at least one of N,N-dimethylformamide, N,N-dimethylacetamide, dimethyl sulfoxide, tetrahydrofuran, chloroform, dichloromethane, toluene, chlorobenzene, o-dichlorobenzene, ethyl acetate, methanol, acetone, acetonitrile, ethylene glycol dimethyl ether, 1,2-dichloroethane, dioxane, pyridine and 2-methylpyrrolidone;
the concentration of the imide compound in the organic solvent is 1-50 mg/mL.

* * * * *